US010548476B2

(12) United States Patent
Lane et al.

(10) Patent No.: US 10,548,476 B2
(45) Date of Patent: Feb. 4, 2020

(54) PATIENT MONITORING SYSTEM

(71) Applicant: Welch Allyn, Inc., Skaneateles Falls, NY (US)

(72) Inventors: John A. Lane, Weedsport, NY (US); Steven D. Baker, Beaverton, OR (US); Rachel Williamson, Batesville, IN (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 77 days.

(21) Appl. No.: 15/679,570

(22) Filed: Aug. 17, 2017

(65) Prior Publication Data

US 2019/0053707 A1   Feb. 21, 2019

(51) Int. Cl.
| | | |
|---|---|---|
| *A61B 5/00* | (2006.01) | |
| *A61B 5/05* | (2006.01) | |
| *G16H 40/67* | (2018.01) | |
| *A61B 5/11* | (2006.01) | |
| *A61G 7/05* | (2006.01) | |
| *G06F 19/00* | (2018.01) | |
| *G16H 10/60* | (2018.01) | |
| *G16H 50/20* | (2018.01) | |

(52) U.S. Cl.
CPC .......... *A61B 5/0022* (2013.01); *A61B 5/0507* (2013.01); *A61B 5/1116* (2013.01); *A61B 5/6891* (2013.01); *A61B 5/7282* (2013.01); *A61G 7/05* (2013.01); *G16H 40/67* (2018.01); *A61B 5/1115* (2013.01); *A61B 5/746* (2013.01); *G06F 19/3418* (2013.01); *G16H 10/60* (2018.01); *G16H 50/20* (2018.01)

(58) Field of Classification Search
CPC ..... A61N 5/0022; A61N 5/7282; A61N 5/746
See application file for complete search history.

(56) References Cited

U.S. PATENT DOCUMENTS

| | | |
|---|---|---|
| 8,761,853 B2 | 6/2014 | Thaveeprungsriporn et al. |
| 8,977,347 B2 | 3/2015 | Mestha et al. |
| 9,020,185 B2 | 4/2015 | Mestha et al. |
| 2007/0060802 A1 | 3/2007 | Ghevondian et al. |
| 2011/0263952 A1 | 10/2011 | Bergman et al. |
| 2013/0019405 A1 | 1/2013 | Flanagan et al. |
| 2013/0345568 A1 | 12/2013 | Mestha et al. |

(Continued)

FOREIGN PATENT DOCUMENTS

| | | |
|---|---|---|
| EP | 2438849 A1 | 4/2012 |
| WO | 2014030091 A1 | 2/2014 |

(Continued)

OTHER PUBLICATIONS

International Search Report and Written Opinion in PCT/2018/043052 dated Nov. 6, 2018, 12 pages.

(Continued)

*Primary Examiner* — Joseph M Dietrich
(74) *Attorney, Agent, or Firm* — Merchant & Gould P.C.

(57) ABSTRACT

A subject monitoring system operates to detect a current status of a subject in a subject arrangement area, such as on a bed, and predict an upcoming status of the subject. The system includes a subject status detection device that may use a radar signal. A radar signal is transmitted toward the subject and is used to detect a subject status, such as a subject position, a subject incontinence condition, and a physiological condition of the subject. One example of the radar signal includes a millimeter wave.

18 Claims, 13 Drawing Sheets

(56) References Cited

U.S. PATENT DOCUMENTS

| | | |
|---|---|---|
| 2014/0275833 A1 | 9/2014 | Vanderpohl, III |
| 2014/0276504 A1 | 9/2014 | Heil et al. |
| 2014/0303454 A1 | 10/2014 | Clifton et al. |
| 2015/0282724 A1 | 10/2015 | McDuff et al. |
| 2015/0302158 A1 | 10/2015 | Morris et al. |
| 2015/0379370 A1 | 12/2015 | Clifton et al. |
| 2018/0078216 A1 | 3/2018 | Baker et al. |

FOREIGN PATENT DOCUMENTS

| | | |
|---|---|---|
| WO | 2015078735 A1 | 6/2015 |
| WO | 2015086338 A1 | 6/2015 |
| WO | 2016092290 A1 | 6/2016 |
| WO | 2016-123287 A1 | 8/2016 |

OTHER PUBLICATIONS

Wu, Hao-Yu et al., "Eulerian Video Magnification for Revealing Subtle Changes in the World," http://people.csail.mit.edu/mrub/papers/vidmag.pdf, Jul. 4, 2012, 8 pages.

Tarassenko, L. et al., "Non-contact vide-based vital sign monitoring using ambient light and auto-regressive models," http://iopscience.iop.org/article/10.1088/0967-3334/35/5/807/meta, Institute of Physics and Engineering in Medicine, 2014, 26 pages.

Chandler, David L., "Your vital signs, on camera," http://news.mit.edu/2010/pulse-camera-1004, Oct. 4, 2010, 3 pages.

PATIENT MONITORING SYSTEM

BACKGROUND

Geriatric patients or those who are incapacitated can be hospitalized for an extended period of time, which can cause such patients to suffer from various problems, such as pressure ulcers and incontinence. Prompt services or treatments are important to cure or prevent such problems. For example, ambulation can be periodically needed to prevent pressure ulcers. It is also important to change an absorbent pad as quickly as possible after the patient leaks urine on the bed. Therefore, it is desirable to monitor such a patient status and provide proper services to the patient while minimizing delay.

SUMMARY

In general terms, the present disclosure relates to a patient monitoring system. In one possible configuration and by non-limiting example, the system includes a subject status detection device that operates to detect a subject status, such as a subject position, a subject incontinence condition, and a physiological condition of the subject. Various aspects are described in this disclosure, which include, but are not limited to, the following aspects.

One aspect is a system for monitoring a subject status. The system includes a subject arrangement area for arranging a subject thereon, a signal transmitter configured to transmit a radar signal toward the subject arranged on the subject arrangement area, a signal receiver configured to receive the radar signal, and a signal analysis device configured to detect a temporal variation of the radar signal and determine a subject status based on the temporal variation.

Another aspect is a method for monitoring a subject status. The method includes arranging a subject in a subject arrangement area, transmitting a radar signal toward the subject, receiving the radar signal, monitoring a temporal variation of the radar signal, and determining a subject status based on the temporal variation.

DETAILED DESCRIPTION

Figure 1:
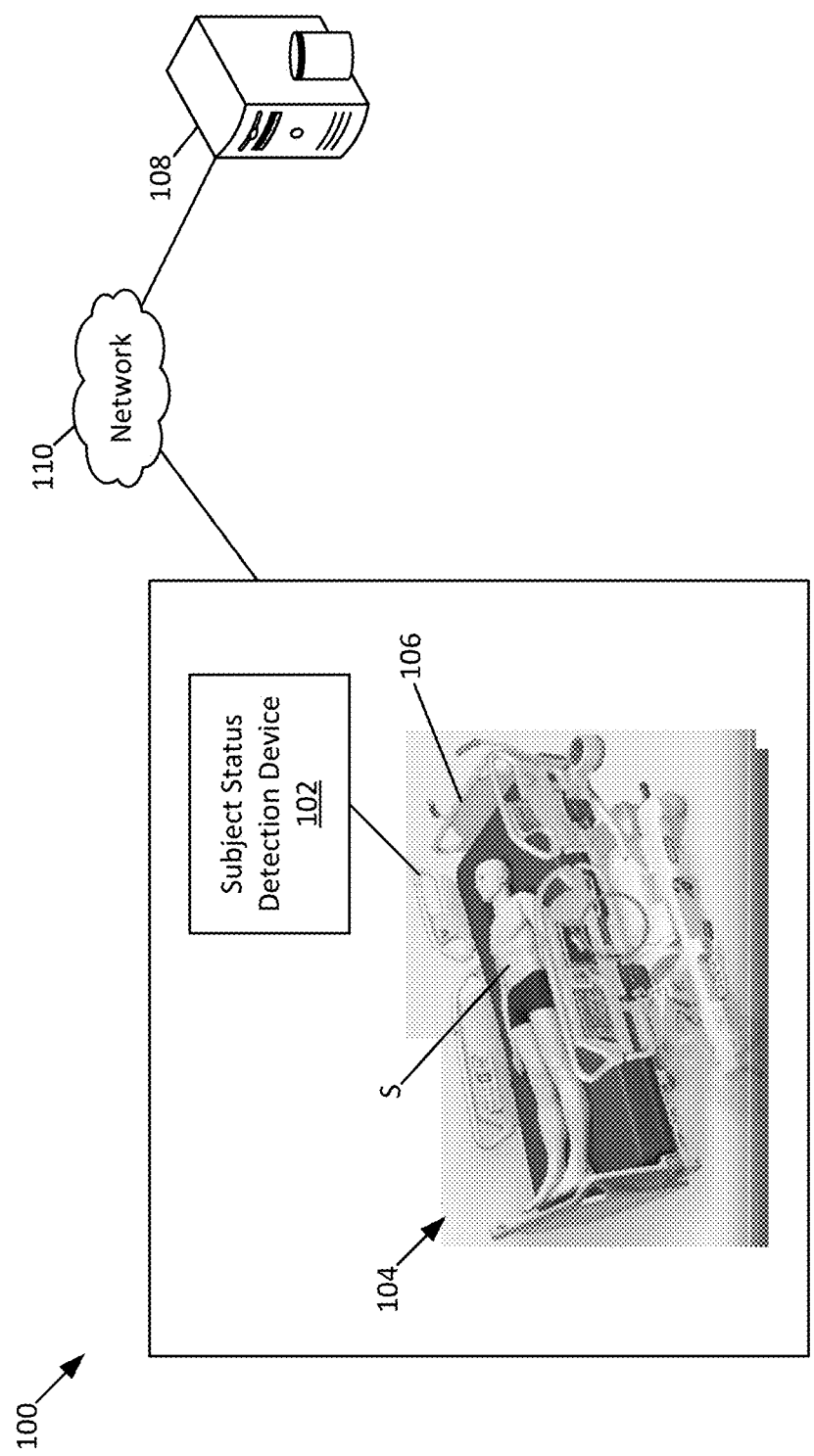
FIG. 1 schematically illustrates an example system for monitoring a subject.

Various embodiments will be described in detail with reference to the drawings, wherein like reference numerals represent like parts and assemblies throughout the several views.

In general, a subject monitoring system of the present disclosure operates to detect a current status of a subject in a subject arrangement area, such as on a bed, and predict an upcoming status of the subject. The system includes a subject status detection device that may use a radar signal. In certain examples, a radar signal is transmitted toward the subject and is used to detect a subject status, such as a subject position, a subject incontinence condition, a subject ambulation, and/or a physiological condition of the subject. One example of the radar signal includes a millimeter wave, such as a signal having a band of spectrum between abound 30 GHz and about 300 GHz. Other examples of the radar signal include microwaves and ultrawideband (UWB).

In certain examples, the system can detect one or more body portions of the patient by analyzing the radar signal and predicting an upcoming position of the patient based on the analysis. For example, the system can predict what the patient wants to do, such as starting ambulating or going to a restroom, by determining the current position of the patient with respect to the patient bed or a temporal change in the position of the patient with respect to the patient bed based on the detected body portions of the patient. In another example, the system can operate to predict a likelihood that a patient falls from a patient bed based on the arrangement of detected body positions. The system can generate a notification to a healthcare practitioner so that the healthcare practitioner assists the patients or prevents the patient's falling from the bed.

In some examples, the system uses rule data for prediction of an upcoming subject position. Such rule data include information about relationship or correlation between current subject status with upcoming subject status.

In certain examples, the system can monitor the returned signals over time and detect abnormalities in the signals to identify a wet spot in the subject arrangement area (such as moisture in an absorbent material of the bed). Detection of a wet spot is used to assist a patient with incontinence, such as urinary incontinence.

FIG. 1 schematically illustrates an example system 100 for monitoring a subject. In this example, the system 100 includes a subject status detection device 102 to monitor a subject S. In some embodiments, the subject S is arranged in a subject arrangement area 104 which is associated with the subject status detection device 102. The subject arrangement area 104 can include a subject support device 106, such as a bed, on which the subject can lie, rest, or sleep. Other examples of the subject support device include lifts, chairs, stretchers, and surgical tables. In this document, the subject support device 106 is also referred to as the bed 106.

In some embodiments, the subject status detection device 102 is arranged at the subject arrangement area 104 and operates to monitor various aspects associated with the subject S, some examples of which include a physical condition of the subject (such as a physical arrangement, movement, posture, position, or the like of the subject), an incontinence condition of the subject, and physiological parameters of the subject. Example operations of the subject status detection device 102 are described herein.

The subject S can be a person, such as a patient, who is clinically treated by one or more healthcare practitioners, and/or one or more guardians, for medical and/or research purposes. Examples of the guardian include a parent of the subject, a family member of the subject, a caregiver of the subject, a primary physician of the subject, and any other interested parties. The healthcare practitioner is a person who provides healthcare service to the subject. Examples of healthcare practitioners include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services. The healthcare practitioner can be an institution, company, business, and/or entity. In other embodiments, the subject S can be an animal or other living organism that can be monitored with the system of the present disclosure. Although the system 100 is primarily described with respect to a single subject, it is understood that a plurality of subjects can be monitored with the system of the present disclosure, either individually or in group.

With continued reference to FIG. 1, in some examples, the subject monitoring system 100 is operable to communicate with a data management system 108 via a data communication network 110. The data management system 108 operates to manage the subject's personal and/or medical information, such as health conditions and other information. The data management system 108 can be operated by the healthcare practitioner and/or a healthcare service provider, such as a hospital or clinic.

Some embodiments of the data management system 108 are configured to communicate with the subject status detection device 102. For example, the subject status detection device 102 and the data management system 108 are connected via the network 110 to transmit various data therebetween. In other examples, the subject status detection device 102 is capable of directly communicating with the data management system 108 to transmit measurement data (and other data associated with the subject S). In some examples, the data management system 108 operates to provide information that can be used to assist the subject S, the guardian and/or the healthcare practitioner to provide suitable healthcare to the subject S. In some examples, the data management system 108 includes such a computing device as described in FIG. 5. Examples of the data management system 108 include Connex® data management systems available from Welch Allyn Inc., Skaneateles Falls, N.Y.

The data communication network 110 communicates digital data between one or more computing devices, such as among the subject status detection device 102 and the data management system 108. Examples of the network 110 include a local area network and a wide area network, such as the Internet. In some embodiments, the network 110 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. A wireless communication system typically includes an optical or RF transmitter for transmitting optical or RF signals, and an optical or RF receiver for receiving optical or RF signals. Examples of wireless communication systems include Wi-Fi communication devices (such as utilizing wireless routers or wireless access points), cellular communication devices (such as utilizing one or more cellular base stations), Bluetooth, ANT, ZigBee, medical body area networks, personal communications service (PCS), wireless medical telemetry service (WMTS), and other wireless communication devices and services.

Figure 2:
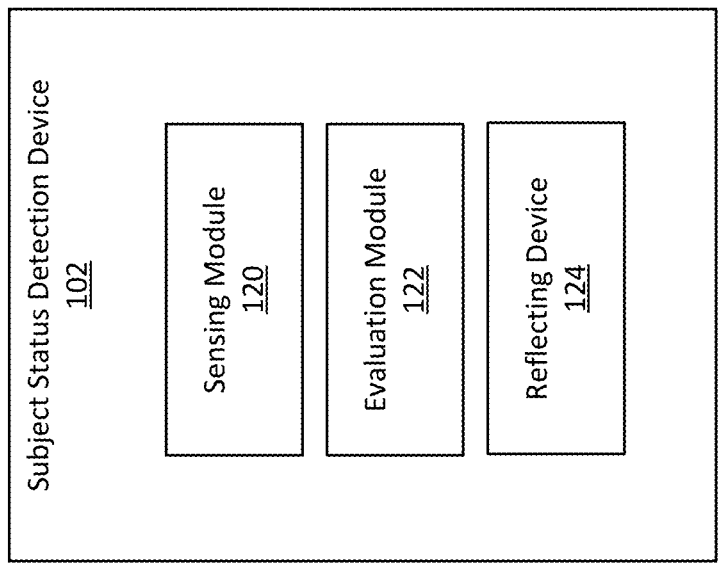
FIG. 2 illustrates an example subject status detection device.

FIG. 2 illustrates an example of the subject status detection device 102. The subject status detection device 102 includes a sensing module 120, an evaluation module 122, and a reflecting device 124.

The sensing module 120 operates to sense a status of the subject arranged in the subject arrangement area. In some embodiments, the sensing module 120 includes a radar signal transceiver to transmit a radar signal toward the subject and receive the reflected signal, which can be used to determine the subject status. An example configuration of the sensing module 120 is described with reference to FIG. 3.

The evaluation module 122 operates to analyze the radar signal and identify the subject status. In some embodiments, the evaluation module 122 is configured integral with the sensing module 120. Various methods used in the evaluation module 112 are described herein in connection with the sensing module 120.

The reflecting device 124 is used to enhance reflection of the radar signal back to the sensing module 120. As described herein, in some embodiments, the reflecting device 124 can include a plurality of reflectors arranged at the subject arrangement area 104 and/or a plurality of reflective elements which can be arranged in the subject arrangement area or worn or carried by the subject. In other embodiments, the reflecting device 124 is not used. For example, other objects or surfaces, such as the subject's surface or the surface associated with incontinence, can reflect signals with or without the reflecting device 124. An example arrangement of the reflecting device 124 is illustrated and described with reference to FIG. 4.

Figure 3:
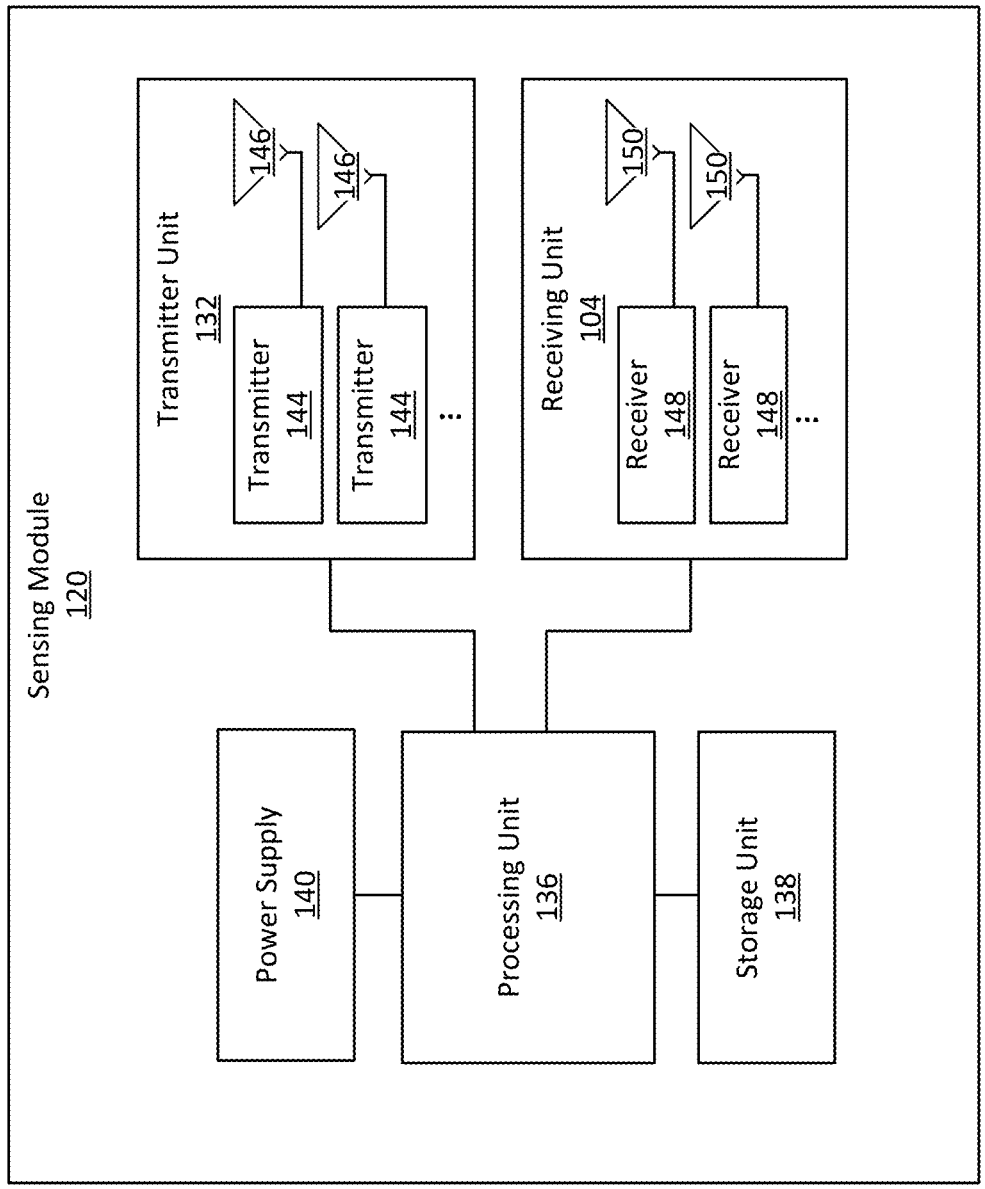
FIG. 3 illustrates an example configuration of a sensing module.

FIG. 3 illustrates an example configuration of the sensing module 120. In this example, the sensing module 120 includes a signal transmitting unit 132, a signal receiving unit 134, a processing unit 136, a storage unit 138, and a power supply 140.

The sensing module 120 can be of various types. In some embodiments, the sensing module 120 is configured as a radar module which uses radio waves to determine various characteristics of objects. In this example, the radar module is configured to detect various aspects of the subject S, as described herein. In some embodiments, the sensing module 120 is configured to incorporate at least some functionalities of the evaluation module 122. One example of the sensing module 120 is IR1642, available from Texas Instruments Inc., Dallas, Tex.

The signal transmitting unit 132 includes one or more transmitters 144 for producing signals, and one or more transmitting antennas 146 for transmitting the signals. The signals from the transmitters reflect off an object (such as the subject S and surrounding objects) and other reflecting elements (such as the reflecting device 124) and return to the signal receiving unit 134. For example, the transmitters 144 emit radar signals (also referred to as radio waves or electromagnetic waves) in predetermined directions through the transmitting antennas 146. When the signals come into contact with objects or reflective elements, the signals are reflected or scattered in many directions. The radar signals can be effectively reflected by materials of considerable electrical conductivity, such as by metals, by seawater, by wet materials or grounds. The radar signals that are reflected back towards the transmitters are the desirable ones that make radar work. If the object is moving either toward or away from the transmitters, there is a slight equivalent change in the frequency of the radio signals, caused by the Doppler effect.

The signal receiving unit 134 includes one or more receivers 148 and one or more receiving antennas 150 for receiving the signals reflected from the object, such as the subject S. In some embodiments, the same antennas can be used for both the receiving antennas 150 and the transmitting antennas 146. In other embodiments, the signal receiving unit 134 is arranged in the same location as, or adjacent to, the signal transmitting unit 132. The reflected signals captured by the receiving antennas can be weak, and can be strengthened by electronic amplifiers and/or signal-processed to recover useful radar signals.

In some embodiments, one or more horn lens antennas can be used to increase signal strength of the target signal or area.

When radar signals travelling though one material meet another material having a different dielectric constant or diamagnetic constant, the signals reflect or scatter from the boundary between the two materials. For example, a solid object in the air or a vacuum, or a significant change in atomic density between the object and what surrounds the object, can scatter the signal from its surface. This is particularly the case for electrically conductive materials such as metal. Radar signals scatter in various ways depending on the wavelength of the signals and the shape of the target object. If the wavelength of a signal is shorter than the size of the target object, the signal can bounce off in a way similar to the way light is reflected by a mirror. If the wavelength is much longer than the size of the target object, the target object may not be visible because of poor reflection.

A plurality of transmitters 144, a plurality of transmitting antennas 145, a plurality of receivers 148, and a plurality of receiving antennas 150 can be used to transmit signals to different directions or angles, and receive reflected signals from different directions or angles, thereby detecting different objects and/or different portions of a single object, which can be used to map different objects and/or different portions of an object within an area that is being monitored by the sensing module 120.

Various types of signals can be used. In one example, the sensing module 120 uses millimeter waves (also referred to as mmWaves or millimeter band), which is the band of spectrum between about 30 GHz and about 300 GHz. Millimeter waves are also known as extremely high frequency (EHF). Millimeter waves have short wavelengths that can range from about 10 millimeters to about 1 millimeter.

Millimeter waves have high atmospheric attenuation and are absorbed by gases in the atmosphere, which reduces the range and strength of the waves over long distances. Moisture (water or humidity) can impact performance and reduce signal strength. In some examples, millimeter waves can be used for sensing, imaging, and communications. Millimeter sensors can measure range, velocity, and angle between the sensors and objects in high accuracy. Millimeter waves can penetrate materials, such as plastic, drywall and clothing, and are highly directions. Millimeter waves have large absolute bandwidths and thus can be used to distinguish two nearby objects.

With still reference to FIG. 3, the processing unit 136 operates to control the signal transmitting unit 132 and the signal receiving unit 134. In some embodiments, the processing unit 135 is further configured to perform the functionalities of the evaluation module 122, such as processing and analyzing of the signals, determining subject status, and predicting upcoming subject status. The processing unit 136 can be implemented in a way known in the art, including, for example, a processor, a decoder, and an encoder.

The storage unit 138 includes one or more memories configured to store data associated with the signals and data usable to evaluate the signals. The storage unit 142 can be of various types, including volatile and nonvolatile, removable and non-removable, and/or persistent media. In some embodiments, the storage unit 142 is an erasable programmable read only memory (EPROM) or flash memory.

In some embodiments, the power supply 140 can be included in the sensing module 120 and provides power to operate the sensing module 120 and associated elements. In some examples, the power supply 140 includes one or more batteries, which is either for single use or rechargeable. In other examples, the power supply 140 includes an external power source, such as mains power or external batteries.

Figure 4:
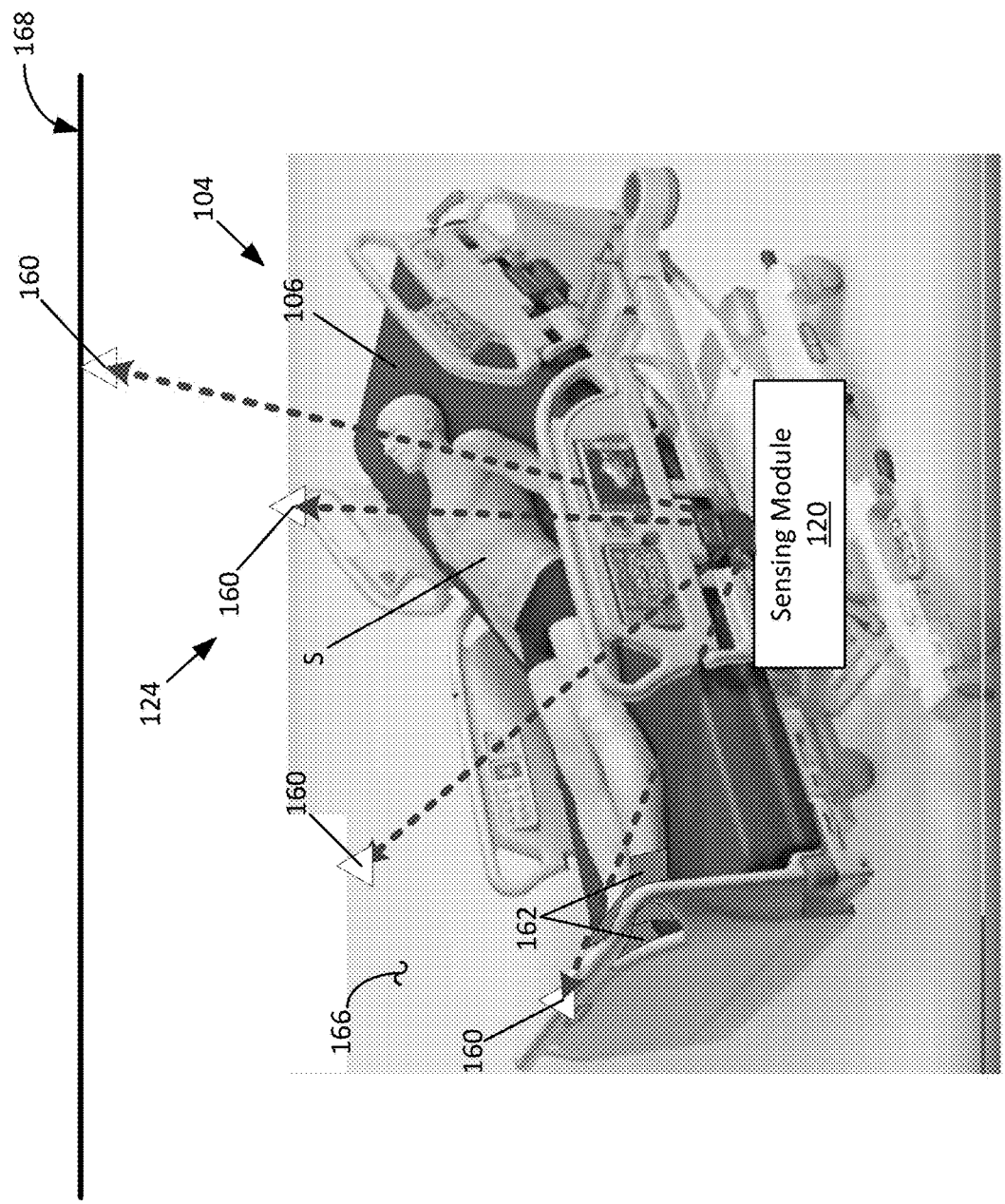
FIG. 4 illustrates an example operation of the sensing module.

FIG. 4 illustrates an example operation of the sensing module 120. In some examples, the sensing module 120 is used with the reflecting device 124.

In some embodiments, the sensing module 120 is arranged in the subject arrangement area 104. The sensing module 120 can be arranged in various locations. In one example, the sensing module 120 is located under the bed 106. In another example, the sensing module 120 is arranged at or around the bed 106, such as at the head of the bed 106, the side of the bed 106, or the foot portion of the bed 106. In yet another example, the sensing module 120 is located away from the bed 106, such as at the wall 166 or ceiling 168 of a room or space including the subject arrangement area 104. Other locations for the sensing module 120 are also possible. In some embodiments, the sensing module 120 (including transmitter and/or receiver) can be configured to automatically or manually move and/or rotate with respect to the bed 106 or other areas to reposition for improved signals.

The reflecting device 124 can be used with the sensing module 120 to improve the reflection of signals transmitted from the sensing module 120. In some embodiments, the reflecting device 124 can include one or more reflectors 160 and other reflective elements 162. The reflectors 160 are configured to reflect radar signals back to the sensing module 120.

The reflectors 160 can be arranged in various locations. The reflectors 160 can be arranged in various locations within the subject arrangement area 104, such as the wall and ceiling of a room or space wherein the subject arrangement area 104 is included. In other examples, the reflectors 160 can be arranged at or around the bed 106, such as the head portion, side portions, and foot portion of the bed and/or under the bed. Other locations of the reflectors are also possible. In some embodiments, the reflectors 160 can be configured to automatically or manually move or be located to calibrate the system.

In some embodiments, the locations of the reflectors 160 can be selected to detect particular portions of the subject being monitored, such as the head, the trunk, the pelvis, and the feet of the subject. For example, the reflectors 160 are arranged around the bed surface such that the signals at least generally pass through predetermined body portions of the subject when transmitted from the sensing module 120 and reflected at the reflectors 160 to return to the sensing module 120. In the illustrated example of FIG. 4, the dotted lines connecting between the sensing module 120 and the reflectors 160 represent signals transmitted from and returning to the sensing module 120, and the signals can generally pass through different body portions, such as the head, the trunk, the pelvis, and the feet of the subject.

The other reflective elements 162 can be made in the form wearable or carried by the subject S. Examples of such wearable reflective elements 162 can be configured as clothing, such as socks, underwear, and gowns, which includes reflective threads. Such wearable reflective elements 162 can be used to identify body portions of the subject associated with the reflective elements 162. By way of example, the hospital typically provides patients with non-slip stockings, and, therefore, such stockings can be used as reflectors to monitor the subject's status (e.g., subject's movement or position) if the stockings are made to contain reflective materials (e.g., metallic threads). Further, other objects or surfaces can work as reflective elements. For example, when the subject incontinence occurs (e.g., leak of urine or other fluid), the subject surface or the bed surface (e.g., an absorbent pad) can become more reflective and function as reflective elements.

Figure 5:
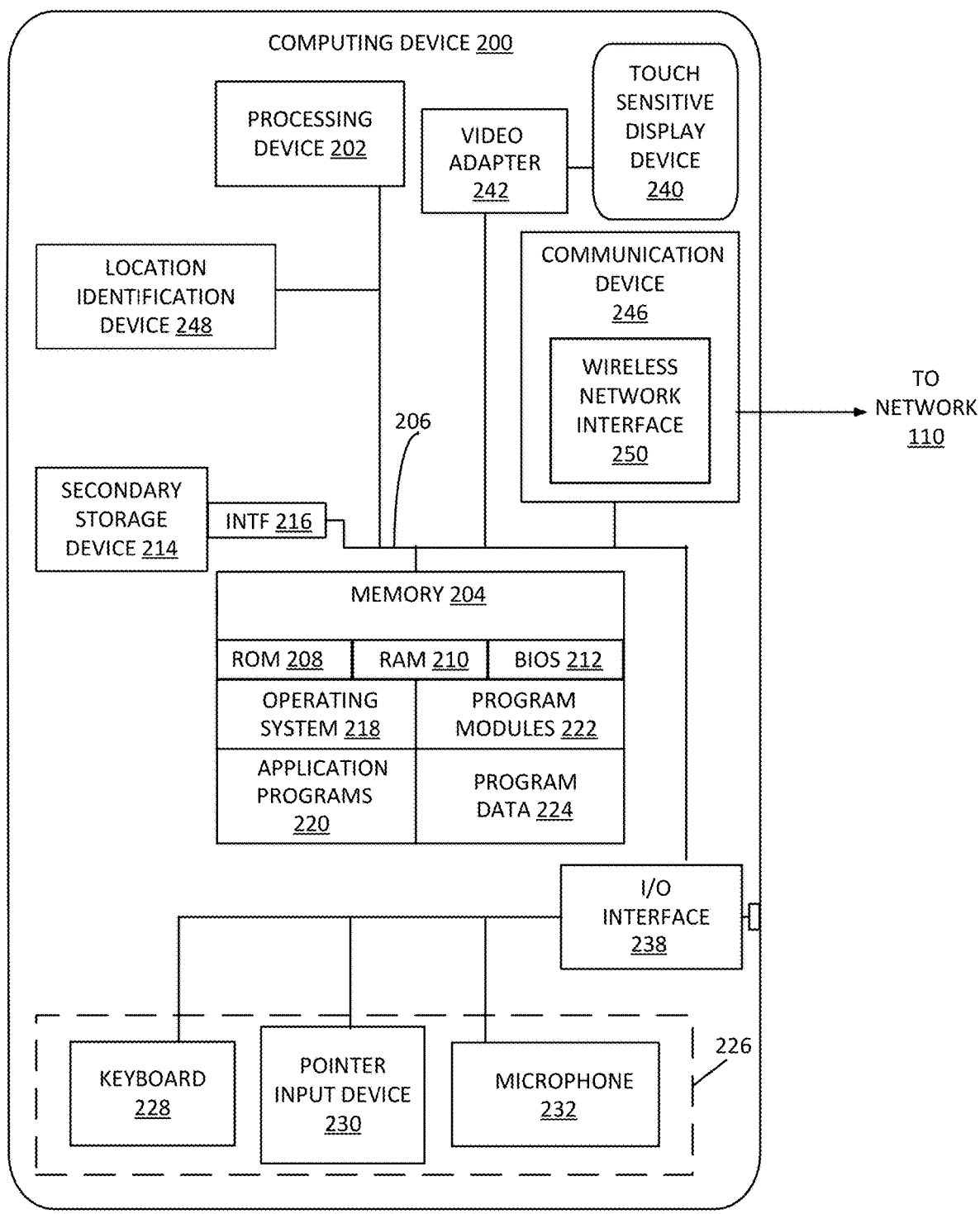
FIG. 5 illustrates an exemplary architecture of a computing device which can be used to implement aspects of the present disclosure.

FIG. 5 illustrates an exemplary architecture of a computing device 200 which can be used to implement aspects of the present disclosure, including the subject status detection device 102 and the data management system 108, and will be referred to herein as the computing device 200. The computing device 200 is used to execute the operating system, application programs, and software modules (including the software engines) described herein. The subject status detection device 102 and the data management system 108 can include all or some of the elements described with reference to FIG. 5, with or without additional elements.

The computing device 200 can be of various types. In some embodiments, the computing device 200 is one or more desktop computers, one or more laptop computers, other devices configured to process digital instructions, or any combination thereof. In other embodiments, the computing device 200 is one or more mobile computing devices. Examples of the computing device 200 as a mobile computing device include a mobile device (e.g., a smart phone and a tablet computer), a wearable computer (e.g., a smartwatch and a head-mounted display), a personal digital assistant (PDA), a handheld game console, a portable media player, a ultra-mobile PC, a digital still camera, a digital video camera, and other mobile devices.

The computing device 200 includes, in some embodiments, at least one processing device 202, such as a central processing unit (CPU). A variety of processing devices are available from a variety of manufacturers, for example, Intel or Advanced Micro Devices. In this example, the computing device 200 also includes a system memory 204, and a system bus 206 that couples various system components including the system memory 204 to the processing device 202. The system bus 206 is one of any number of types of bus structures including a memory bus, or memory controller; a peripheral bus; and a local bus using any of a variety of bus architectures.

The system memory 204 includes read only memory 208 and random access memory 210. A basic input/output system 212 containing the basic routines that act to transfer information within the computing device 200, such as during start up, is typically stored in the read only memory 208.

The computing device 200 also includes a secondary storage device 214 in some embodiments, such as a hard disk drive, for storing digital data. The secondary storage device 214 is connected to the system bus 206 by a secondary storage interface 216. The secondary storage devices and their associated computer readable media provide nonvolatile storage of computer readable instructions (including application programs and program modules), data structures, and other data for the computing device 200.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 214 or memory 204, including an operating system 218, one or more application programs 220, other program modules 222, and program data 224.

In some embodiments, the computing device 200 includes input devices to enable a user to provide inputs to the computing device 200. Examples of input devices 226 include a keyboard 228, a pointer input device 230, a microphone 232, and a touch sensitive display 240. Other embodiments include other input devices. The input devices are often connected to the processing device 202 through an input/output interface 238 that is coupled to the system bus 206. These input devices 226 can be connected by any number of input/output interfaces, such as a parallel port, serial port, game port, or a universal serial bus. Wireless communication between input devices and interface 238 is possible as well, and includes infrared, BLUETOOTH® wireless technology, 802.11a/b/g/n, cellular, or other radio frequency communication systems in some possible embodiments.

In this example embodiment, a touch sensitive display device 240 is also connected to the system bus 206 via an interface, such as a video adapter 242. The touch sensitive display device 240 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 240, the computing device 200 can include various other peripheral devices (not shown), such as speakers or a printer.

The computing device 200 further includes a communication device 246 configured to establish communication across the network. In some embodiments, when used in a local area networking environment or a wide area networking environment (such as the Internet), the computing device 200 is typically connected to the network through a network interface, such as a wireless network interface 250. Other possible embodiments use other wired and/or wireless communication devices. For example, some embodiments of the computing device 200 include an Ethernet network interface, or a modem for communicating across the network. In yet other embodiments, the communication device 246 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The computing device 200 typically includes at least some form of computer-readable media. Computer readable media includes any available media that can be accessed by the computing device 200. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 200. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device 200 illustrated in FIG. 5 is also an example of programmable electronics, which may include one or more such computing devices, and when multiple computing devices are included, such computing devices can be coupled together with a suitable data communication network so as to collectively perform the various functions, methods, or operations disclosed herein.

Referring again to FIG. 5, the computing device 200 can include a location identification device 248. The location identification device 248 is configured to identify the location or geolocation of the computing device 200. The location identification device 248 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Figure 6:
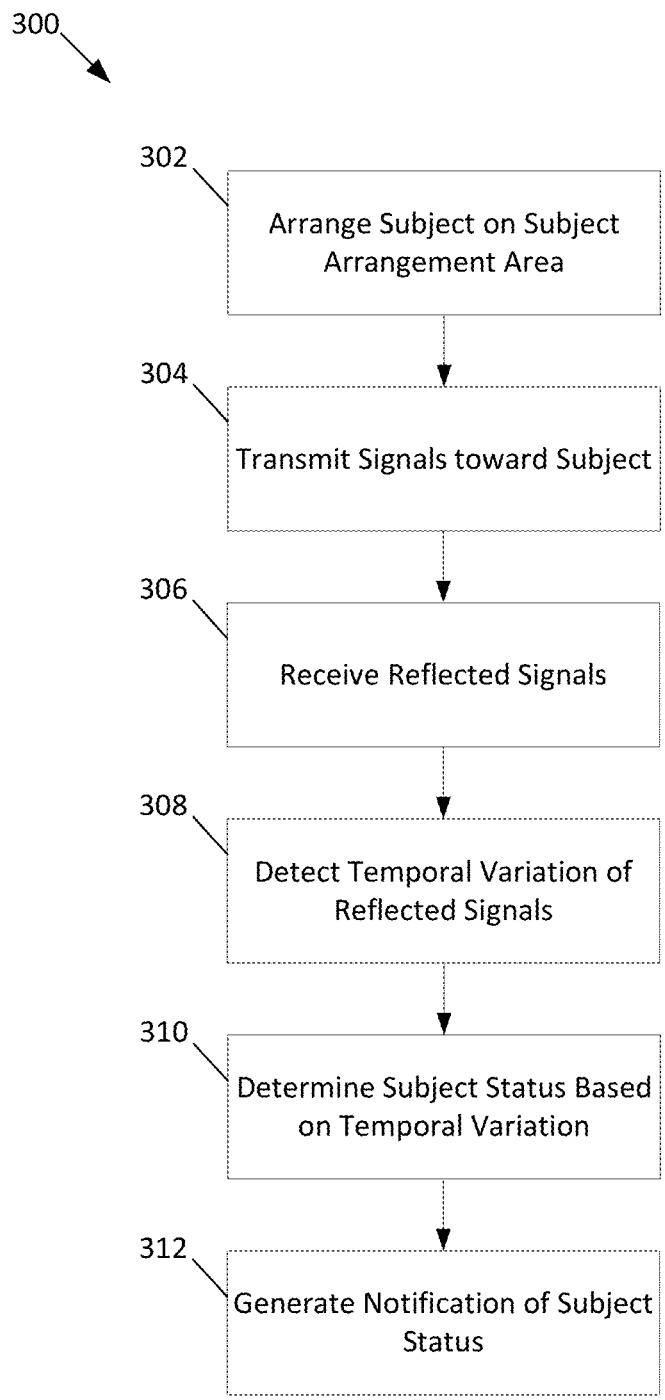
FIG. 6 illustrates an example method for monitoring a subject.

FIG. 6 illustrates an example method 300 for monitoring a subject. In some embodiments, the method 300 is performed using the system 100. The method 300 can begin at operation 302 in which a subject S is arranged on the subject arrangement area 104. In some embodiments, a bed 106 is provided to the subject S when the subject S is hospitalized for treatment. As described herein, the subject status detection device 102 is arranged at or around the subject arrangement area 104 to monitor the subject.

At operation 304, the subject status detection device 102 operates to transmit one or more signals toward the subject. As described herein, the sensing module 120 can be used to generate and transmit the signals. The signals can reflect, scatter, and/or pass through, the subject and at least partially return to the subject status detection device 102, such as the sensing module 120.

At operation 306, the subject status detection device 102 receives the reflected signals. The reflected signals can include signals reflected from the subject S, the bed 106, and any other objects surrounding the subject S or the bed 106, such as the walls or ceiling of a room or space including the subject arrangement area 104 and other people around the subject arrangement area 104 (for example, visitors, healthcare practitioners, or other people standing by the bed 106).

In some embodiments, the reflected signals can be used to determine the locations of different body portions of the subject and/or different things surrounding the subject S. For example, a plurality of signals is separately transmitted toward predetermined directions or angles to identify particular body portions of the subject. In other embodiments, the reflected signals can be used to determine an outline of the subject and/or what surrounds the subject. For example, the reflected signals are used for mapping of the subject and/or the surrounding objects.

At operation 308, the subject status detection device 102 operates to detect a temporal variation of the reflected signals. In some embodiments, the subject status detection device 102 monitors the reflected signals at two different times (such as the reflected signals at a first time and the reflected signals at a second time later than the first time), and compares the reflected signals to determine a change between the reflected signals at the first time and the reflected signals at the second time. In other embodiments, the subject status detection device 102 periodically monitors the reflected signals and determines a change in the reflected signals over time. In yet other embodiments, the subject status detection device 102 continuously monitors the reflected signals and determines a change in the reflected signals over time. In some embodiments, discrete measurements at Nyquist frequency or higher can be considered continuous. In other embodiments, discrete measurements of subject position or condition, such as incontinence, which occur at an interval shorter than a clinically significant period (e.g., 30 seconds for incontinence monitoring) can be considered continuous. Other methods are also possible to detect the temporal variation of the reflected signals.

At operation 310, the subject status detection device 102 operates to determine a subject status based on the detected temporal variation. In some embodiments, the temporal variation of the reflected signals is representative of a change in various conditions of the subject S over time, and such a change in the subject's conditions can be used to detect the subject's current status or predict the subject's future status. Examples of the subject status, which can be determined by the subject status detection device 102, are described in more detail with reference to FIG. 7.

At operation 312, the subject status detection device 102 operates to generate a notification of the subject status. The notification can be delivered to a healthcare practitioner, the subject, and/or other people or entities that are interested in the subject's status. The notification can be over various types, such as visual, audible, and/or textile. For example, the notification is generated on a computing device operated or carried by the healthcare practitioner, the subject, or other people. Other forms of the notification are also possible.

Figure 7:
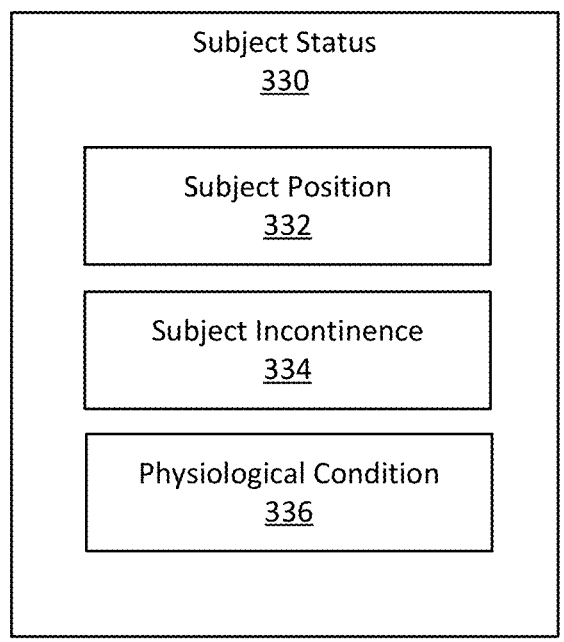
FIG. 7 illustrates examples subject status monitored by the system.

FIG. 7 illustrates examples of the subject status 330 that can be monitored by the subject status detection device 102. In some embodiments, the subject status 330 includes a subject position 332, a subject incontinence condition 334, and a subject's physiological condition 336.

The subject position 332 relates to a physical condition of the subject, such as arrangement, location, movement, posture, pose, or physical characteristics of the subject. In some embodiments, the subject position 332 includes the subject's location or movement on the surface of the bed 106 or with respect to the bed 106. For example, when the subject stays on a bed 106, the subject status detection device 102 can operate to monitor the subject position 332 and determine whether the subject remains in a desired position or predict what the subject is doing or wants to do based on the detected subject position 332. A few examples of the subject position 332 include lying on the back, lying on the side, lying on the back, sitting on the side of the bed, sitting on the bed, leaning the truck on a raised section of the bed, lying with the feet raised, lying with the head raised, and moving for ambulation. An example operation of the subject status detection device 102 for monitoring the subject position 332 is described in more detail with reference to FIGS. 8-10.

The subject incontinence condition 334 includes the condition regarding the subject's incontinence. For example, when the subject suffers from urinary incontinence, the subject status detection device 102 can monitor the subject and determine if there is leakage of urine from the subject. By way of example, the subject status detection device 102 is used to detect a wet spot or a region with moisture built up on or around the subject. An example operation of the subject status detection device 102 for monitoring the subject incontinence condition 334 is described in more detail with reference to FIGS. 11-13.

The physiological condition 336 includes various physiological parameters of the subject. Physiological parameters can include vital signs, physiological measurements, and biological measurements, which can be detected from various portions of the subject's body. For example, physiological parameters include measurements of the body's basic functions, which are useful in detecting or monitoring medical problems. Examples of physiological parameters include body temperature, pulse rate (i.e., heart rate), respiration rate (i.e., breathing rate), blood pressure, blood gas, and SpO2.

Body temperature can be taken in various manners, such as orally, rectally, by ear, or by skin. The pulse rate is a measurement of the heart rate, or the number of times the heart beats per minute. The pulse rate can also indicate a heart rhythm and the strength of the pulse. The pulse can be taken on different body portions where the arteries are located, such as on the side of the neck, on the side of the elbow, or at the wrist. The respiration rate is the number of breaths a person takes per minute and is used to note whether the person has any difficulty breathing. Blood pressure is the force of the pushing against the artery walls. There may be other vital signs, such as pain, Glasgow coma scale, pulse oximetry, blood glucose level, end-tidal $CO_2$, functional status, shortness of breath, and gait speed.

In some embodiments, the subject status detection device 102 is used for ballistocardiography, which is detection of minute motions of the body that occur due to the motion of blood through the body. In other embodiments, the subject status detection device 102 is arranged and configured to transmit a radar signal toward the heart of a subject and detect a heartbeat based on the reflected signal. In other embodiments, the subject status detection device 102 is used to detect various vital signs with or without the functionality of detecting the subject position 332 and/or the subject incontinence condition 334.

Figure 8:
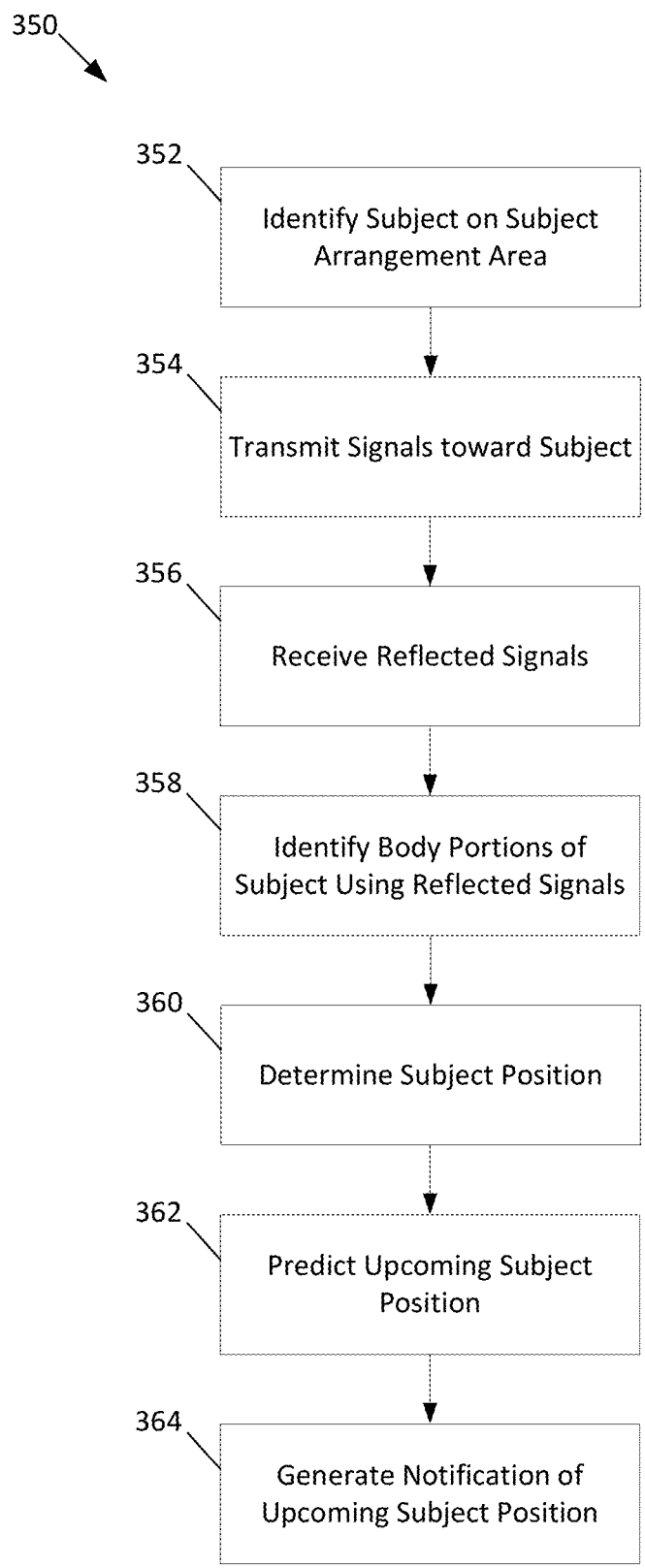
FIG. 8 is a flowchart of an example method for monitoring a subject position as the subject status.

FIG. 8 is a flowchart of an example method 350 for monitoring the subject position 332 as the subject status 330. In this example, it is primarily described that the subject status detection device 102 operates to perform the method 350. In other examples, one or more other computing devices, such as the data management system 108, can be used to at least partially perform the method 350 with or without the cooperation of the subject status detection device 102.

The method 350 can begin at operation 352 in which the subject status detection device 102 operates to identify a subject S arranged in the subject arrangement area 104. For example, the subject status detection device 102 identifies that a subject S exists on the bed 106. In some embodiments, the subject status detection device 102 can transmit a radar signal and receive a reflected signal, and then evaluate the reflected signal to determine the existence of the subject in the subject arrangement area 104.

At operation 354, the subject status detection device 102 transmits a radar signal toward the subject. In some embodiments, the subject status detection device 102 transmits a plurality of signals in different directions or angles toward the subject. As described herein, in some embodiments, the plurality of signals can be used to identify different body portions of the subject or generate an outline of the subject.

At operation 356, the subject status detection device 102 receives the reflected signals. In some embodiments, the reflecting device 124 (such as a plurality of reflectors 160 or reflective elements 162) is used to improve the reflection of the signals transmitted from the subject status detection device 102.

At operation 358, the subject status detection device 102 operates to identify body portions of the subject based on the reflected signals. In some embodiments, the reflected signals are received from different directions or at different angles and can represent different body portions of the subject. For example, a signal that has been reflected at or adjacent the head of the subject can be used to identify the position of the head of the subject, and a signal that has been reflected at or adjacent the pelvis of the subject can be used to identify the pelvis of the subject.

In some embodiments, the phase of the reflected signal can be used to determine a motion toward or away from the radar. When the radar sends out a signal periodically and receives the reflected signal, the reflected signal can be used to determine whether it has returned with phase shifts, and then determine vital signs, breath respirations, or other subject conditions or positions based on the phase shifts.

At operation 360, the subject status detection device 102 operates to determine the subject position based on the identified body portions of the subject. In some embodiments, the subject status detection device 102 evaluates the relative positions or arrangements of at least some of the identified body portions of the subject and determines how the subject is positioned. By way of example, the subject status detection device 102 can determine whether the subject is lying on the front, back, or side, or sitting on the bed surface or at the edge of the bed, based on the relative arrangements of the body portions of the subject.

In some embodiments, the subject status detection device 102 operates to generate an outline of the subject based on the identified body portions of the subject. For example, data points indicating the body portions of the subject are mapped and/or extrapolated to generate the outline of the subject. In some examples, the generated outline of the subject can be used to determine the subject position.

Figure 10A:
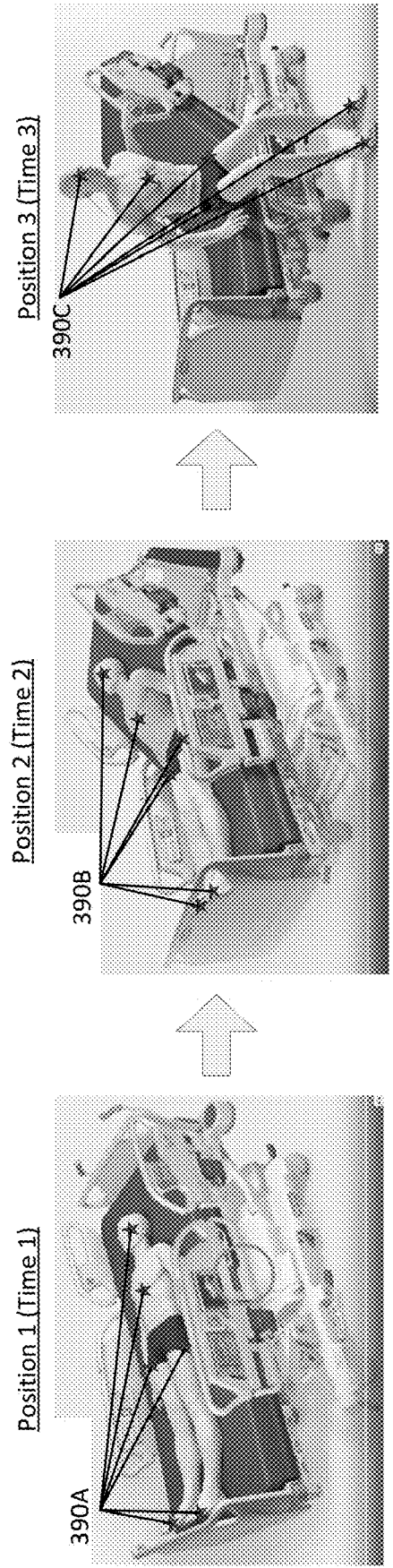
FIG. 10A illustrates example subject body points detected at different times.

At operation 362, the subject status detection device 102 operates to predict an upcoming subject position based on the determined subject position. For example, the subject status detection device 102 can determine what position the subject will move to, based on the determined subject position. By way of example, as illustrated in FIG. 10A, when the subject is determined to have Position 2, the subject status detection device 102 can predict the subject is moving to a sitting position (for example, either by raising the upper body away from the bed surface or raising a section of the bed from a flat position).

In some embodiments, the subject status detection device 102 can use rule data to determine the upcoming subject position. In some embodiments, the rule data can be pre-generated and saved in a storage device of the subject status detection device 102 or other computing devices, such as the data management system 108. Such rule data can include information correlating a set of current subject positions with a set of future subject positions. In addition, the rule data can further consider environmental factors in correlating current subject positions with future subject positions.

For example, a time of the day can be considered. By way of example, when the subject is identified to be currently sitting on the bed edge at night, it can be predicted that the subject is getting out of the bed and wants to go to a rest room. In another example, when the subject's current position is determined to be a sitting position on the bed edge during daytime, it can be predicted that the subject is getting out of the bed for ambulation. In yet another example, if the subject's current position is identified as moving (e.g., rolling) toward the edge of the bed while being lying on the bed, it can be predicted that the subject is about to fall from the bed.

At operation 364, the subject status detection device 102 can generate a notification of the upcoming subject position. In some embodiments, the notification can be provided to a healthcare practitioner so that the healthcare practitioner can determine what the subject is doing or what the subject wants to do, and take necessary actions before the subject asks for such actions. By way of example, upon receiving a notification of the upcoming subject position, a healthcare practitioner can come to the subject and assist the subject with what the subject wants to do, such as going to a restroom or performing ambulation, or prevent the subject from falling from the bed.

Figure 9:
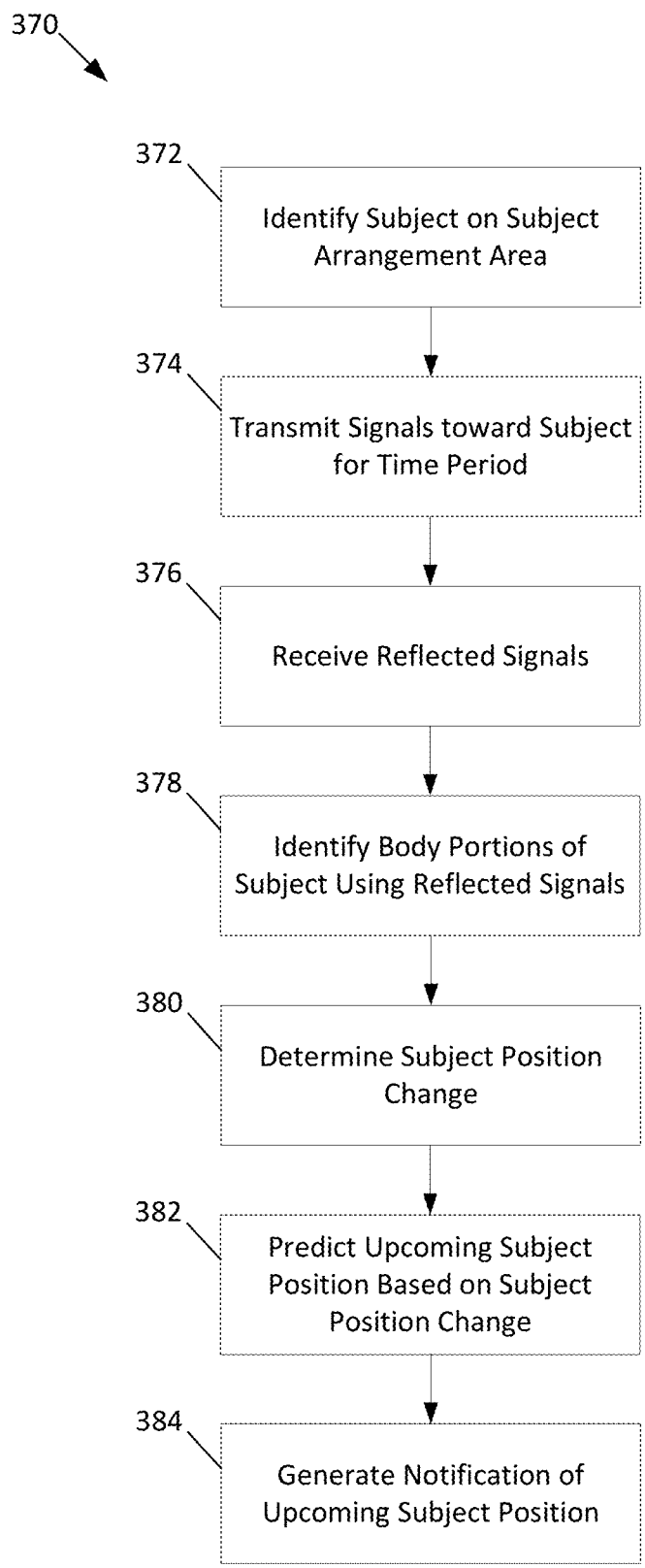
FIG. 9 is a flowchart of another example method for monitoring the subject position as the subject status.

FIG. 9 is a flowchart of another example method 370 for monitoring the subject position 332 as the subject status 330. In this example, it is primarily described that the subject status detection device 102 operates to perform the method 370. In other examples, one or more other computing devices, such as the data management system 108, can be used to at least partially perform the method 370 with or without the cooperation of the subject status detection device 102.

The method 370 can begin at operation 372 in which the subject status detection device 102 operates to identify a subject S arranged in the subject arrangement area 104. For example, the subject status detection device 102 identifies that a subject S exists on the bed 106. In some embodiments, the subject status detection device 102 can transmit a radar signal and receive a reflected signal, and then evaluate the reflected signal to determine the existence of the subject in the subject arrangement area 104.

At operation 374, the subject status detection device 102 transmits a radar signal toward the subject for a predetermined time. In some embodiments, the subject status detection device 102 transmits a plurality of signals in different directions or angles toward the subject. As described herein, in some embodiments, the plurality of signals can be used to identify different body portions of the subject or generate an outline of the subject.

In some embodiments, the subject status detection device 102 transmits a signal at intervals. For example, a signal is periodically transmitted. In other embodiments, a signal is transmitted at a first time, and the same signal is transmitted at a second time after the first time. In yet other embodiments, a signal is transmitted over time. For example, the subject status detection device 102 continuously transmits a signal for a predetermined time.

At operation 376, the subject status detection device 102 receives the reflected signals. In some embodiments, the reflecting device 124 (such as a plurality of reflectors 160 or reflective elements 162) is used to improve the reflection of the signals transmitted from the subject status detection device 102.

At operation 378, the subject status detection device 102 operates to identify body portions of the subject based on the reflected signals. In some embodiments, the reflected signals are received from different directions or at different angles and can represent different body portions of the subject. For example, a signal that has been reflected at or adjacent the head of the subject can be used to identify the position of the head of the subject, and a signal that has been reflected at or adjacent the pelvis of the subject can be used to identify the pelvis of the subject.

As illustrated in FIG. 10A, the subject status detection device 102 detects a first set of body points 390A at a first time (T1). The first set of body points 390A is detected using the reflected signals received at or around the first time (T1) and used to identify the body portions of the subject at the first time (T1). Similarly, the subject status detection device 102 detects a second set of body points 390B at a second time (T2). The second set of body points 390B is detected using the reflected signals received at or around the second time (T2) and used to identify the body portions of the subject at the second time (T2). Further, the subject status detection device 102 detects a third set of body points 390C at a third time (T3). The third set of body points 390C is detected using the reflected signals received at or around the third time (T3) and used to identify the body portions of the subject at the third time (T3). In this example, the body points 390A, 390B, 390C are used to identify the head, trunk, pelvis, and feet of the subject.

In some embodiments, the subject status detection device 102 operates to generate an outline of the subject based on the identified body portions of the subject. For example, data points indicating the body portions of the subject are mapped and/or extrapolated to generate the outline of the subject. In some examples, the generated outline of the subject can be used to determine the subject position.

Figure 10B:
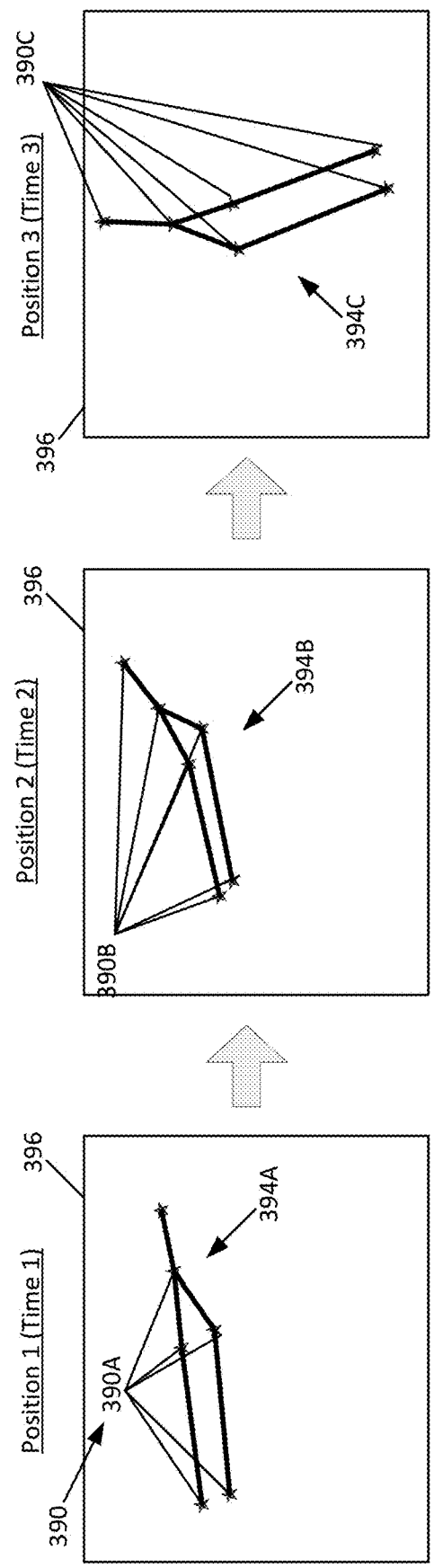
FIG. 10B illustrates example outlines of the subject generated at different times.

In the illustrated example of FIG. 10B, the subject status detection device 102 operates to generate a model 394 of a portion or all of the subject's body using the body points 390 (including 390A, 390B, and 390C) at a particular time (such as T1, T2, or T3). In some examples, the model 394 can be created as a three-dimensional model or two-dimensional model. By way of example, a first model 394A is constituted by mapping the first set of body points 390A at the first time (T1), and used to represent a subject position 332 of the subject at the first time (T1). The arrangement of the first model 394A can indicate that the subject is lying on the bed 106.

For example, the configuration or shape of the first model 394A that is horizontally arranged and substantially flat in a map 396 can represent that the subject is lying, and the relative position of the first model 394A within the map 396, in which the first model 394A is located at an upper portion of the map 396, can show that the subject stays on the bed 106. A second model 394B is mapped from the second set of body points 390B at the second time (T2), and used to represent a subject position 332 of the subject at the second time (T2).

The arrangement of the second model 394B can indicate that the subject is generally sitting on the bed 106 or lying with the torso raised. For example, the configuration or shape of the second model 394B, in which the body points corresponding to the head and trunk are higher than the body points corresponding to the pelvis and the feet, can represent that the subject is generally sitting or leaning to a raised head section of the bed, and the relative position of the second model 394B within the map 396, in which the second model 394B stays at an upper portion of the map 396, can show that the subject remains on the bed 106.

A third model 394C is generated by mapping the third set of body points 390C at the third time (T3), and used to represent a subject position 332 of the subject at the third time (T3). The arrangement of the third model 394C can indicate that the subject is generally standing or sitting on the edge of the bed. For example, the configuration or shape of the third model 394C, in which the body points are generally arranged vertically in the map 396, can represent that the subject is generally standing or sitting on the bed edge, and the relative position of the third model 394C within the map 396, in which the third model 394C extends vertically in the map 396, can also indicate that the subject is substantially standing.

At operation 380, the subject status detection device 102 operates to determine a change of the subject position based on the identified body portions of the subject for a predetermined time. In some embodiments, the subject status detection device 102 tracks a change in the positions or arrangements of at least some of the identified body portions of the subject and determines the movement of the subject body over time. In the illustrated example of FIGS. 10A and 10B, the subject status detection device 102 can monitor a change in the body model 394 (including 394A, 394B, and 394C) over time (such as from T1 to T3), and determine that the subject may be in the course of getting out of the bed.

At operation 382, the subject status detection device 102 operates to predict an upcoming subject position based on the subject position change as determined at operation 380. For example, the subject status detection device 102 can determine what position the subject will move to, based on the determined subject position. The upcoming subject position can be a subject's intended movement. By way of example, as illustrated in FIGS. 10A and 10B, the subject status detection device 102 can monitor Positions 1, 2, and 3 of the subject over time and predict that the subject is getting out of the bed.

In some embodiments, the subject status detection device 102 can use rule data to determine the upcoming subject position. Such rule data can include information correlating a set of subject position changes with a set of future subject positions. In some embodiments, the rule data can be pre-generated and saved in a storage device of the subject status detection device 102 or other computing devices, such as the data management system 108. In addition, the rule data can further consider environmental factors in correlating subject position changes with future subject positions. For example, a time of the day can be considered, such that, when the subject's position is determined to be moving from a lying down position on the bed to a sitting position on the bed edge (from Position 1 to Position 3 in FIG. 10A) at night, it can be predicted that the subject is getting out of the bed and wants to go to a restroom. In another example, when the subject's position is determined to move from a lying down position on the bed to a sitting position on the bed edge (from Position 1 to Position 3 in FIG. 10A) during daytime, it can be predicted that the subject is getting out of the bed for ambulation.

At operation 384, the subject status detection device 102 can generate a notification of the upcoming subject position. In some embodiments, the notification can be provided to a healthcare practitioner so that the healthcare practitioner can determine what the subject is doing or what the subject wants to do, and take necessary actions before the subject asks for such actions.

Figure 11:
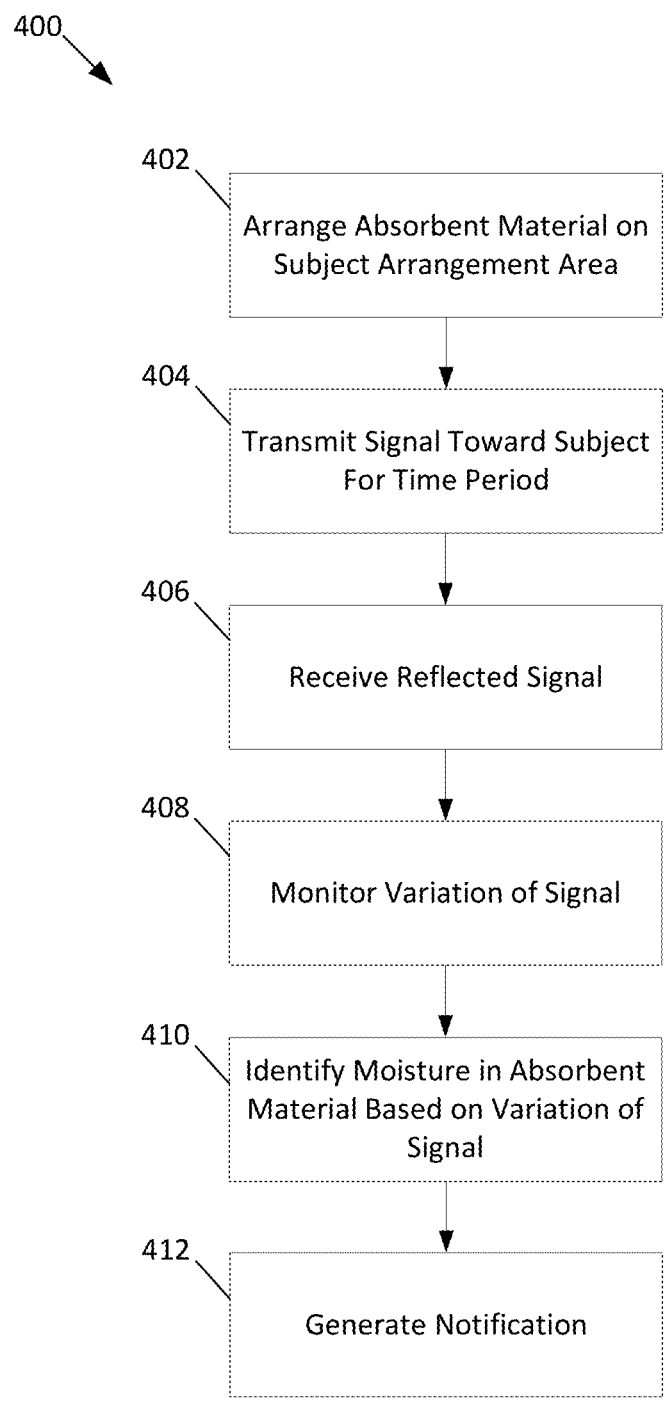
FIG. 11 is a flowchart of an example method for monitoring a subject incontinence as the subject status.
Figure 12:
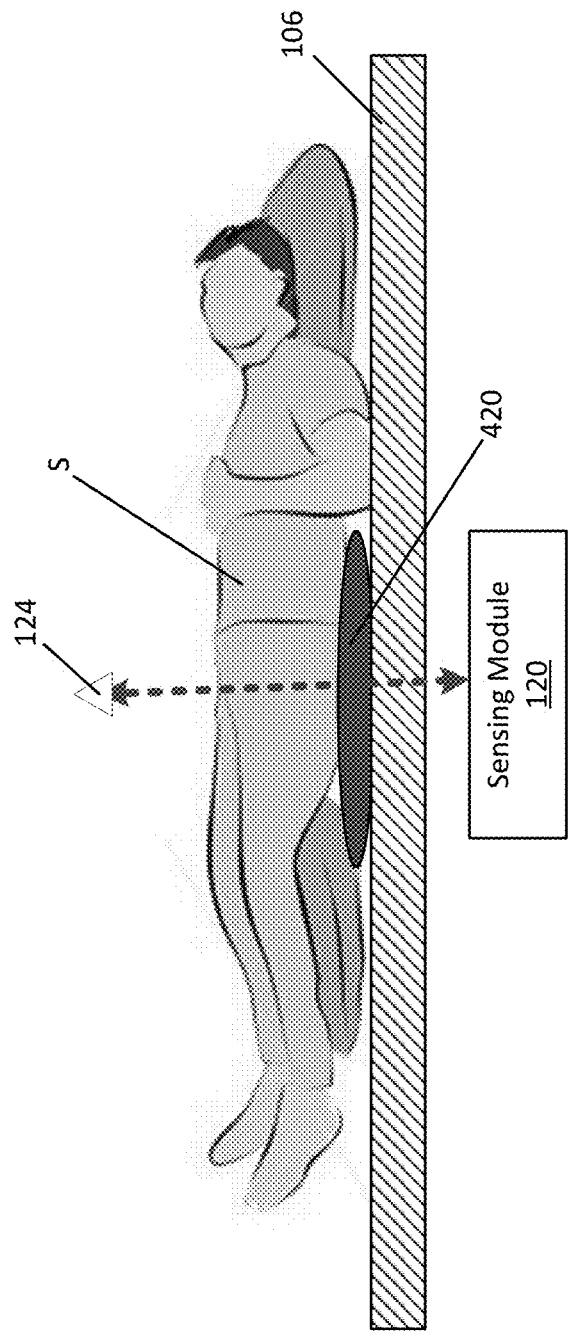
FIG. 12 illustrates an example arrangement of an absorbent material with respect to a subject.

FIG. 11 is a flowchart of an example method 400 for monitoring the subject incontinence condition 334 as the subject status 330. In this example, it is primarily described that the subject status detection device 102 operates to perform the method 400. In other examples, one or more other computing devices, such as the data management system 108, can be used to at least partially perform the method 400 with or without the cooperation of the subject status detection device 102. The method 400 is described with also reference to FIG. 12.

The method 400 can begin at operation 402 in which an absorbent material 420 (FIG. 12) is arranged on the subject arrangement area 104. The absorbent material is configured to absorb a liquid, such as urine, sweat, water, or other liquid forms from a subject, and clean up the subject arrangement area 104. In some embodiments, the absorbent material 420 includes an absorbent pad arranged on the bed 106 and under the subject S. In other embodiments, the absorbent material 420 is incorporated in a mattress of the bed 106 or a frame of the bed 106. In yet other embodiments, the absorbent material 420 is any materials that can absorb moisture or liquid from the subject. Examples of such materials include any absorbable surfaces of the bed, any components (e.g., pads) of a mattress on the bed, any bedclothes or bedding elements (e.g., bed sheet, pillows, pillowcase, blankets, and pads).

At operation 404, the subject status detection device 102 transmits a radar signal towards the subject for a predetermined time. The subject status detection device 102 transmits a signal so that the signal at least partially passes through the absorbent material 420. In some embodiments, the reflecting device 124 is arranged such that the transmitted signal is reflected thereat and returns to the subject status detection device 102.

In some embodiments, the subject status detection device 102 transmits a signal at intervals. For example, a signal is periodically transmitted. In other embodiments, a signal is transmitted at a first time, and the same signal is transmitted at a second time after the first time. In yet other embodiments, a signal is transmitted over time. For example, the subject status detection device 102 continuously transmits a signal for a predetermined time.

At operation 406, the subject status detection device 102 receives the reflected signal. In some embodiments, the reflecting device 124 (such as a plurality of reflectors 160 or reflective elements 162) is used to improve the reflection of the signals transmitted from the subject status detection device 102.

Figure 13:
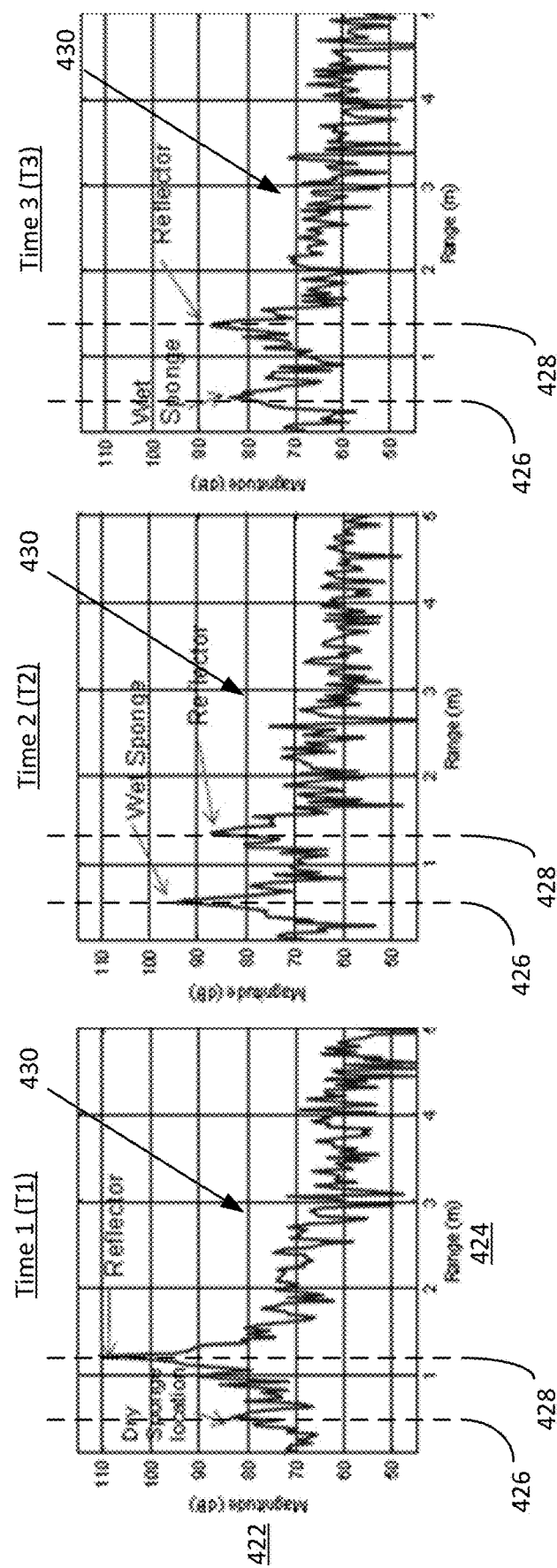
FIG. 13 illustrates example characteristics of signals detected at different times.

At operation 408, the subject status detection device 102 monitors a variation of the signal over time. In some embodiments, the magnitude of the signal is monitored to determine a change in the signal over time. By way of example, as illustrated in FIG. 13, the magnitude of signal 422 along the range of signal 424 are detected over time, such as at a first time (T1), a second time (T2), and a third time (T3). A first range 426 of the signal 430 is associated with, and representative of, a location where the absorbent material 420 is arranged, and a second range 428 of the signal 430 is associated with, and representative of, a location of the reflecting device 124. As the time passes from T1 to T3, the absorbent material 420 contains more liquid. As the liquid content in the absorbent material 420 changes, the magnitude of the signal at the first range 426 also changes. Further, the change in the liquid content of the absorbent material 420 can also cause a change in the magnitude of the signal at the second range 428, as depicted in FIG. 13.

At operation 410, the subject status detection device 102 identifies moisture in the absorbent material 420 based on the variation of the signal. In some embodiments, the subject status detection device 102 determines whether the signal meets one or more predetermined criteria (such as whether the signal exceeds a predetermined threshold). For example, when the signal exceeds such a threshold, the absorbent material 420 is considered to contain a particular amount of moisture or liquid, which may indicate that a liquid, such as urine, has been leaked from the subject. By way of example, as illustrated in FIG. 14, such a threshold includes a predetermined magnitude of the signal at one or more predetermined ranges of the signal (such as the first range 426 and/or the second range 428 of the signal).

At operation 412, the subject status detection device 102 can generate a notification when the absorbent material 420 is determined to contain a predetermined level of moisture. In some embodiments, the notification can be provided to a healthcare practitioner so that the healthcare practitioner can take necessary actions, such as to change the absorbent material 420 or take the subject to a bath room.

In some embodiments, the subject monitoring system of the present disclosure can operate to detect the position or movement of other objects surrounding the subject S, independently or in addition to the monitoring of the subject. For example, the system of the present disclosure can detect a position of a bed rail and predict what the subject is going to do. By way of example, a patient should lower the bed rail before getting out of the bed, and thus it is predictable that the patient wants to leave the bed when a lowered position of the bed rail is detected. In other examples, the system of the present disclosure can be configured to begin monitoring the subject position only when the bed rail is lowered.

In some embodiments, the system of the present disclosure can be used along with a camera system for monitoring the subject status. Visible or infrared cameras can be arranged around the subject and monitor the subject position, incontinence condition, and various physiological conditions. Such cameras can be operated independently or together with the subject monitoring system as described herein, thereby improving the subject monitoring system.

The system of the present disclosure can be configured to distinguish the subject from other people around the subject, such as healthcare practitioners, visitors, or other people standing by the subject. The same or similar methods can be used to identify the subject among other people. For example, the subject position, such as typical positions or arrangements of a patient with respect to a patient bed, can be used to distinguish the subject from non-patient people or objects. Further, the system can operate to measure a subject motion based on, for example, Doppler shift of the signals. Moreover, the system can be used to perform subject tracking. Once the subject is identified, the subject's range and angle to the radar may be compared to new, suddenly different target information. The tracking algorithm can then have two targets at different ranges and angles, which can be analyzed to track the subject.

The system of the present disclosure can further operate as a sleep tracker based on the detected subject position. For example, the system can determine that the subject is sleeping on the bed when the subject position remains horizontally flat (such as Position 1 in FIG. 10A) for a predetermined time. Other parameters, such as vital signs (e.g., lower respiration rate), can also be used to monitor whether the subject is sleeping.

The system of the present disclosure can be configured to distinguish the signals associated with the subject and other noises, such as bed shaking. In some embodiments, the system evaluates the frequencies of the received signals and filters the signals having frequencies which are representative of the noises.

Although the system of the present disclosure is primarily described herein with a patient bed, it is understood that the system may be similarly used for other applications where vitals and/or position data need to be monitored, such as in a car seat, train driver, pilot, and other situations. Further, the system can be used to trigger a signal that can override artificial intelligence in various applications.

The various examples and teachings described above are provided by way of illustration only and should not be construed to limit the scope of the present disclosure. Those skilled in the art will readily recognize various modifications and changes that may be made without following the examples and applications illustrated and described herein, and without departing from the true spirit and scope of the present disclosure.

What is claimed is:

1. A system for monitoring a subject status, the system comprising:
   a subject arrangement area for arranging a subject thereon;
   a signal transmitter configured to transmit a radar signal toward the subject arranged on the subject arrangement area;
   a signal receiver configured to receive the radar signal; and
   a signal analysis device configured to detect a temporal variation of the radar signal and determine a subject status based on the temporal variation, wherein the subject status includes a subject position, and wherein the signal analysis device is further configured to predict an upcoming position of the subject based on the temporal variation.

2. The system of claim 1, wherein the signal analysis device is configured to identify at least one body portion of the subject based on the received radar signal.

3. The system of claim 1, wherein the signal analysis device is further configured to generate an outline of the subject using the received radar signal.

4. The system of claim 1, wherein the subject status includes a subject incontinence condition.

5. The system of claim 1, wherein the subject status includes a physiological condition of the subject.

6. The system of claim 1, further comprising:
a reflector associated with the subject and configured to reflect the radar signal from the signal transmitter.

7. The system of claim 1, wherein the radar signal has a band of spectrum between 30 GHz and 300 GHz.

8. The system of claim 1, wherein the radar signal has a wavelength ranging between 10 mm to 1 mm.

9. The system of claim 1, wherein the subject arrangement area includes a patient bed.

10. The system of claim 1, wherein the signal transmitter and the signal receiver are integrally configured as a signal transceiver.

11. The system of claim 1, wherein the signal analysis device is configured to generate a notification of the subject status to a healthcare practitioner.

12. The system of claim 1, wherein the subject position is determined by detecting a first set of body points at a first time, the first set of body points detected from reflected radar signals received from different directions.

13. The system of claim 12, wherein the signal analysis device is further configured to determine a motion of the subject by detecting a second set of body points at a second time, and tracking changes between the first set of body points and the second set of body points.

14. A method for monitoring a subject status, the method comprising:
arranging a subject in a subject arrangement area;
transmitting a radar signal toward the subject;
receiving the radar signal;
monitoring a temporal variation of the radar signal; and
determining a subject status based on the temporal variation, wherein the subject status includes a subject position, and determining the subject status includes predicting an upcoming status of the subject based on the temporal variation.

15. The method of claim 14, further comprising:
identifying at least one body portion of the subject based on the received radar signal.

16. The method of claim 14, wherein the subject status includes a subject incontinence condition.

17. The method of claim 16, wherein determining a subject status includes:
determining a moisture in the subject arrangement area.

18. A system for monitoring a subject status, the system comprising:
a processing device configured to control operation of the system;
a signal transmitter configured to transmit a radar signal having a band of spectrum between 30 GHz and 300 GHz;
a signal receiver configured to receive the radar signal; and
a computer readable storage medium storing software instructions that, when executed by the processing device, cause the system to:
transmit the radar signal toward a subject using the signal transmitter;
receive the radar signal using the signal receiver;
identify at least one body portion of the subject based on the received radar signal;
monitor a temporal variation of the radar signal;
predict an upcoming status of the subject based on the temporal variation, wherein the upcoming status includes a subject position; and
determine a wet spot around the subject based on the temporal variation.

* * * * *